(12) United States Patent
Rossen et al.

(10) Patent No.: US 7,481,215 B2
(45) Date of Patent: Jan. 27, 2009

(54) DEVICE FOR MIXING ANESTHETIC VAPOR WITH ANESTHETIC GAS

(75) Inventors: Thomas Rossen, Lübeck (DE); Karl-Ludwig Gippert, Lübeck (DE); Michael Heidschmidt, Lübeck (DE); Jürgen Müller, Lübeck (DE); Rainer Kunz, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 557 days.

(21) Appl. No.: 11/190,313

(22) Filed: Jul. 27, 2005

(65) Prior Publication Data

US 2006/0090750 A1 May 4, 2006

(30) Foreign Application Priority Data

Oct. 30, 2004 (DE) .................. 10 2004 052 731

(51) Int. Cl.
*A61M 15/00* (2006.01)
*A61M 16/10* (2006.01)

(52) U.S. Cl. .................. 128/203.12; 128/203.14; 128/203.25; 128/203.26; 128/203.27; 128/204.21; 128/204.22

(58) Field of Classification Search ............ 128/203.12, 128/203.14, 203.25, 203.26, 203.27, 204.21, 128/204.22

See application file for complete search history.

(56) References Cited

U.S. PATENT DOCUMENTS

| 3,420,232 A | 1/1969 | Bickford |
| 5,671,729 A * | 9/1997 | Moll et al. ............. 128/203.14 |

FOREIGN PATENT DOCUMENTS

EP 0 469 797 B2 2/1992

* cited by examiner

*Primary Examiner*—Patricia Bianco
*Assistant Examiner*—Nihir Patel
(74) *Attorney, Agent, or Firm*—McGlew & Tuttle, P.C.

(57) ABSTRACT

An anesthetic evaporator with a pressure control circuit has a differential pressure pick-up (18) can be calibrated in a simple manner. A switchover device (20) is provided according to the present invention at a bypass gap (3), which is designed to connect the gas inlet (4) directly with the gas outlet (5) via a first bypass line (23) and to bridge over the bypass gap (3) via a second bypass line (26) connected to a ventilation duct (27) in a first switching position. The gas flow from the gas inlet (4) to the gas outlet (5) is established via the bypass line (2) in a second switching position. The calibration of the differential pressure pick-up (18) with the pneumatic connections (16, 17) is performed in the first switching position of the switchover means (20) via the ventilation duct (27), which is open toward the ambient atmosphere.

20 Claims, 3 Drawing Sheets

DEVICE FOR MIXING ANESTHETIC VAPOR WITH ANESTHETIC GAS

CROSS REFERENCE TO RELATED APPLICATIONS

This application claims the benefit of priority under 35 U.S.C. § 119 of German Application 10 2004 052 731.8 filed Oct. 30, 2004, the entire contents of which are incorporated herein by reference.

FIELD OF THE INVENTION

The present invention pertains to a device for mixing anesthetic vapor with anesthetic gas.

BACKGROUND OF THE INVENTION

A device of the above-mentioned type has become known from U.S. Pat. No. 3,420,232. Saturated anesthetic vapor from an evaporator chamber is mixed with the anesthetic gas via a dispensing means in the anesthetic evaporator operating according to the bypass principle in order to provide a predetermined concentration of anesthetic in the anesthetic gas. The anesthetic evaporator is provided with a shut-off valve, which is designed to block the gas flow from the evaporator chamber in a first switching position, so that the anesthetic gas flows via a bypass line from a gas inlet to a gas outlet. In a second switching position, the gas flow is released via the evaporator chamber and anesthetic vapor can be mixed with the anesthetic gas by means of the dispensing device. The shut-off valve comprises a lower part, which is provided with gas ducts and is part of the evaporator housing, and a rotatably movable upper part, which is attached thereto and has kidney-shaped gas ducts. Depending on the angular position of the upper part, the kidney-shaped gas ducts of the upper part connect corresponding gas ducts in the lower part, so that a gas flow is released via the shut-off valve or the gas ducts in the lower part are closed.

The upper part has a carrier pin, which is connected with the anesthetic concentration setting member. The shut-off valve is closed in the zero position of the setting member and the anesthetic gas flows via the bypass line directly from the gas inlet to the gas outlet. If the setting member is set from the zero position to a certain anesthetic concentration, the shut-off valve opens above the carrier pin and the gas flow from the evaporator chamber is released.

A certain system pressure must be maintained within the anesthetic tank in case of anesthetics with low boiling point in order to prevent the anesthetic from boiling. A pressure control circuit with a differential pressure sensor and a proportional valve is usually used for the dispensing branch in such evaporators. The carrier gas, which is to be enriched with anesthetic vapor, now flows from a gas inlet to a gas outlet over a first throttle set in a fixed manner, a so-called bypass gap. The anesthetic, which is in the form of a vapor, is mixed with the carrier gas behind the first throttle. The anesthetic evaporated in an evaporator chamber is sent for this purpose via a proportional valve and a second throttle adjustable by the user by means of a setting member. The differential pressure is detected with the differential pressure pick-up upstream of the first throttle and the second throttle. The pressure in front of the second throttle is set with the proportional valve such that the pressure difference equals, on average, zero and an anesthetic concentration that is independent from the gas flow of the carrier gas can thus be set.

An anesthetic evaporator of the type mentioned has become known from EP 469 797 B2. The differential pressure pick-up, which is needed for the pressure control, must be calibrated at regular intervals in order to compensate drift effects. Provisions are made for this purpose for the pneumatic connections of the differential pressure pick-up to be connected with a common pressure source via a separate switchover means, and the common pressure source may also be at atmospheric pressure.

SUMMARY OF THE INVENTION

The basic object of the present invention is to provided a device of the above-mentioned type that makes possible the simple calibration of the differential pressure pick-up.

According to the invention, an anesthetic evaporator is provided with a gas inlet for carrier gas, a gas outlet and a bypass line with a first throttle as a bypass gap between the gas inlet and the gas outlet. An evaporator chamber is provided for a liquid evaporator. A duct extends from the evaporator chamber via a second throttle to the gas outlet. A differential pressure pick-up is provided for detecting the differential pressure upstream of the first throttle and the second throttle between the bypass line and the duct. A ventilation duct is provided that is open toward the environment. A switchover means at the first throttle is designed to connect the gas inlet directly with the gas outlet via a first bypass line and to bridge over the first throttle via a second bypass line connected to the ventilation chamber in a first switching position. In the second switching position the switchover means establishes the gas flow from the gas inlet to the gas outlet via the bypass line.

The advantage of the present invention is essentially that the switchover means is arranged in parallel to the bypass gap in the bypass line. This switchover means is used to connect the gas inlet for the carrier gas via a first bypass line with the gas outlet in a first switching position and at the same time to bring the pneumatic connections of the differential pressure pick-up to atmospheric pressure level via a second bypass line and a ventilation line that is open to the ambient atmosphere. The calibration of the differential pressure pick-up can thus be performed without being affected by the carrier gas flow.

In a second switching position of the switchover means, the gas flow is established through the bypass gap and anesthetic vapor can be mixed with the carrier gas.

It is especially advantageous that a switchover means, which is present anyway and is used to send the carrier gas flow past the throttle means directly from the gas inlet to the gas outlet in a zero position of the anesthetic evaporator, can also be used at the same time for the calibration of the differential pressure pick-up. No additional components are now needed for these functions.

The bypass gap is bridged over in the first switching position of the switchover means, so that the carrier gas can flow directly from the gas inlet to the gas outlet without an increase in flow resistance. This has an especially advantageous effect on a series connection of different anesthetic evaporators, which can be put into operation only individually by means of a blocking device.

An exemplary embodiment is shown in the drawings and will be explained in greater detail below. The various features of novelty which characterize the invention are pointed out with particularity in the claims annexed to and forming a part of this disclosure. For a better understanding of the invention, its operating advantages and specific objects attained by its

DESCRIPTION OF THE PREFERRED EMBODIMENT

Figure 1:
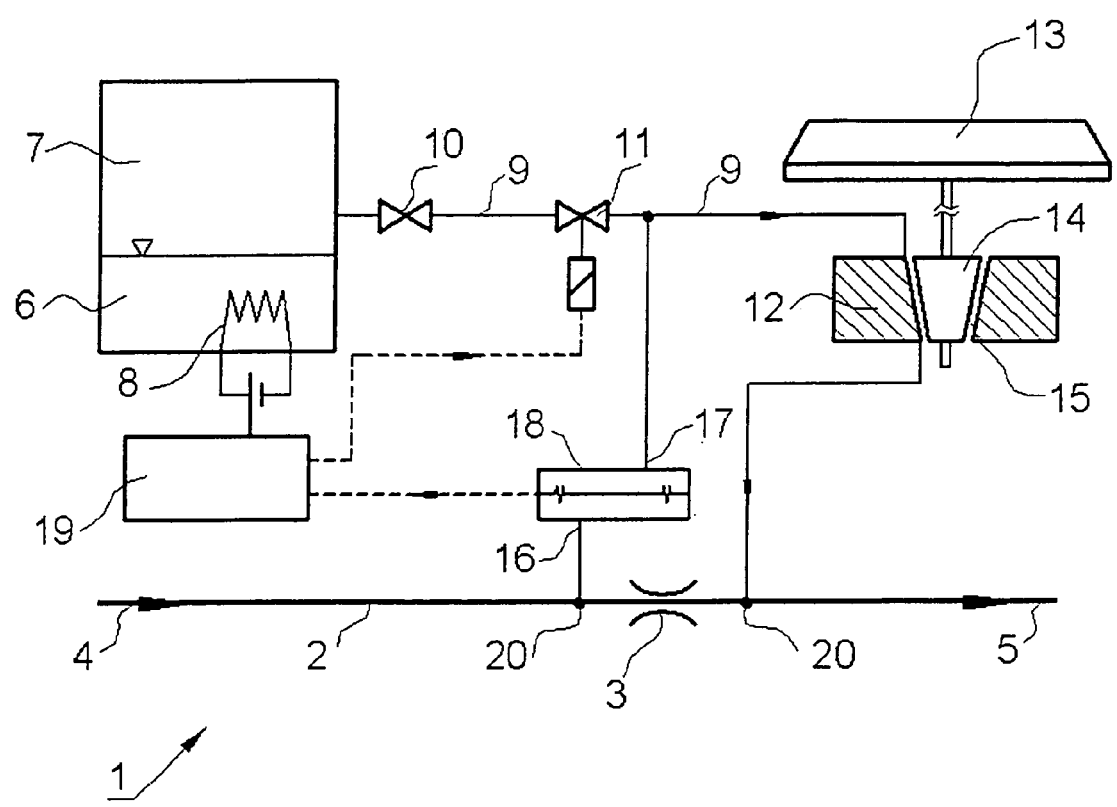
FIG. 1 is a schematic view showing the design of an anesthetic evaporator according to the invention.

Referring to the drawings in particular, FIG. 1 schematically shows the design of an anesthetic evaporator 1, in which the carrier gas flows from a gas inlet 4 to a gas outlet 5 via a bypass line 2. A fixed first throttle 3 is disposed in bypass line 2 acting as a bypass gap. An evaporator chamber 7 is partially filled with liquid anesthetic 6 and is heated to an operating temperature with a heater 8. This delivers anesthetic vapor, which is mixed with the carrier gas stream downstream of the first throttle 3 via a duct 9 with a shut-off valve 10, with a proportional valve 11 and an adjustable second throttle 12.

The second throttle 12 comprises a setting member 13 for the anesthetic concentration and a valve cone 14. The valve cone 14 is displaceable in a valve seat 15 by means of the setting member 13 in such a way that it is able to perform lifting movements and in the vertical direction. Depending on the position of the valve cone 14 in relation to the valve seat 15, a corresponding gap width is set and a gas flow of anesthetic vapor, which is associated therewith, is set.

The pneumatic connections 16, 17 of a differential pressure pick-up 18 are connected to the duct 9 and the bypass line 2 upstream of the first throttle 3 and the second throttle 12. A control unit 19 forms a pressure control circuit together with the heater 8, the proportional valve 11 and the differential pressure pick-up 18 acting as an actual value transducer in order to set identical pressure conditions in the duct 9 and in the bypass line 2 by means of the proportional valve 11. A switchover means 20, which is located upstream and downstream on the first throttle 3, is illustrated in FIGS. 2 and 3.

Figure 2:
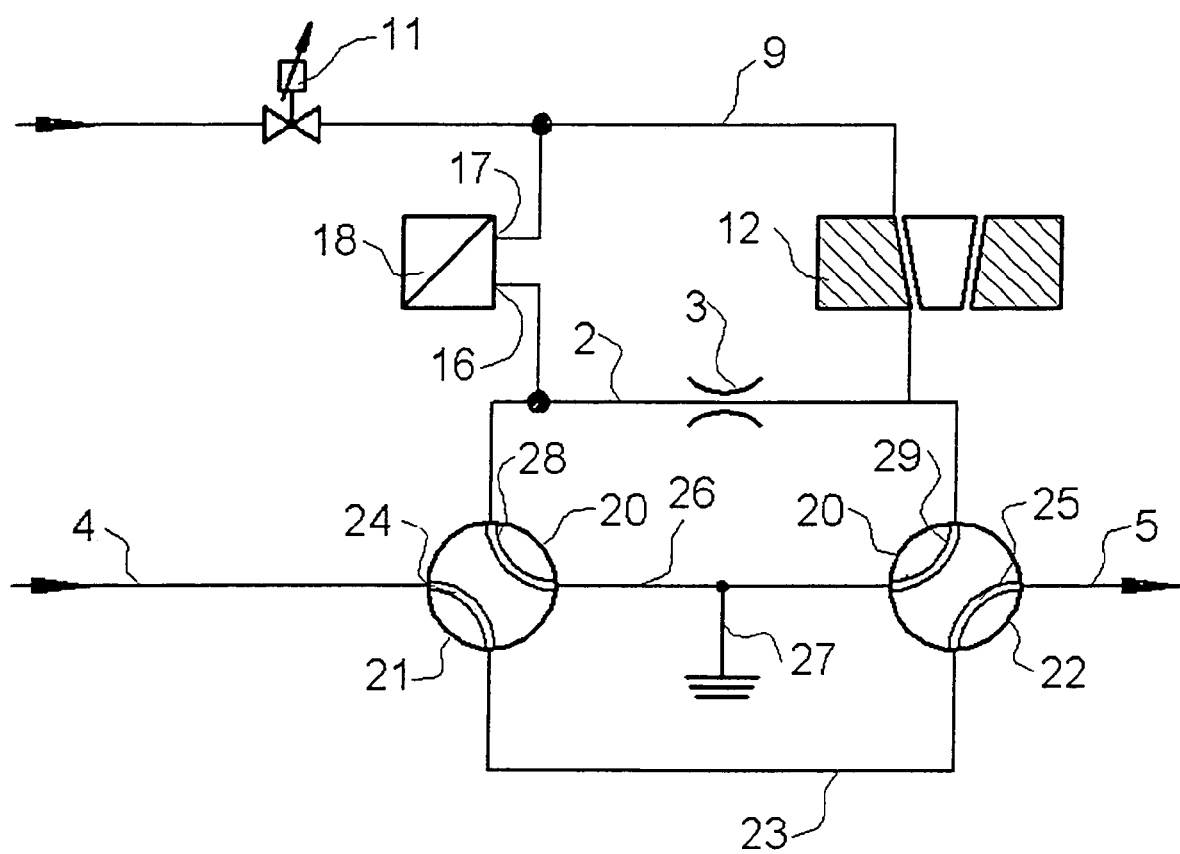
FIG. 2 is a schematic view showing a switchover means according to FIG. 1 in a first switching position.
Figure 3:
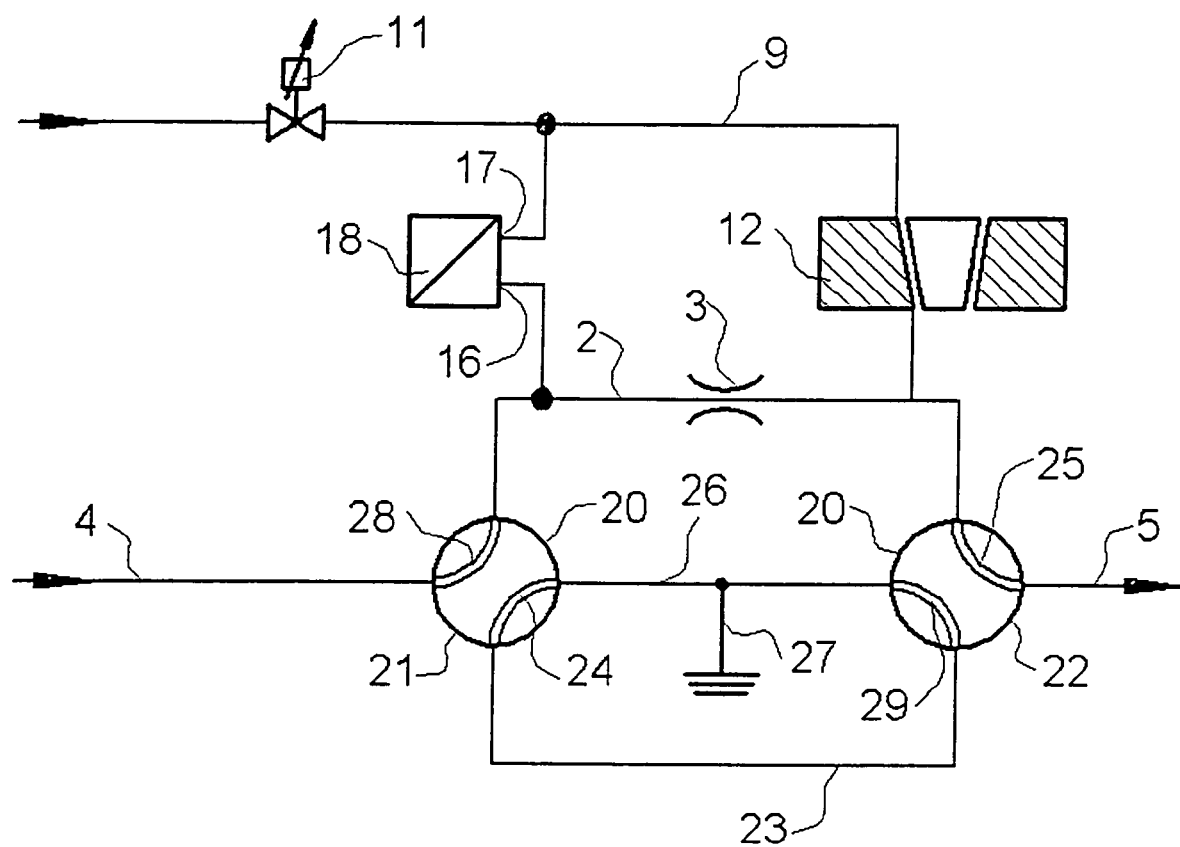
FIG. 3 is a schematic view showing the switchover means according to FIG. 2 in a second switching position.

FIG. 2 shows the switchover means 20 with a first changeover switch 21 and with a second changeover switch 22 in a first switching position, in which the carrier gas flows from the gas outlet 4 via a first bypass line 23 to the gas outlet 5. Identical components are designated by the same reference numbers as in FIG. 1.

The changeover switches 21, 22 contain gas ducts 24, 25, via which the gas flow from the gas inlet 4 to the gas outlet 5 is made possible via the first bypass line 23.

A second bypass line 26 with a ventilation duct 27, which is open toward the environment, is connected with the bypass line 2 and with the first throttle 3 via gas ducts 28, 29 of the changeover switches 21, 22.

In the first switching position of the switchover means 20, the first pneumatic connection 16 of the differential pressure pick-up 18 is connected to the ventilation duct 27 via the bypass line 2, the gas ducts 28, 29 and the first bypass line 26. The path of the gas in the second pneumatic connection 17 likewise extends to the ventilation duct 27 via the duct 9, the second throttle 12, the bypass line 2 and the gas ducts 28, 29. Thus, unaffected by the gas flow of the carrier gas, both pneumatic connections 16, 17 of the differential pressure pick-up 18 are at the atmospheric pressure level.

FIG. 3 shows the second switching position of the switchover means 20, in which the ventilation duct 27 is connected with the bypass lines 23, 26 via the gas ducts 24, 29 and is thus uncoupled from the bypass line 2. The gas flow of the carrier gas extends over the gas ducts 25, 28 from the gas inlet 4 via the bypass line 2 to the gas outlet 5 and can be enriched with anesthetic vapor via the second throttle 12.

While specific embodiments of the invention have been shown and described in detail to illustrate the application of the principles of the invention, it will be understood that the invention may be embodied otherwise without departing from such principles.

What is claimed is:

1. An anesthetic evaporator comprising:

a gas inlet for a carrier gas;

a gas outlet;

a first bypass line with a first throttle defining a bypass gap between the gas inlet and the gas outlet;

a liquid evaporator with an evaporator chamber;

an evaporator duct extending from the evaporator chamber via a second throttle to the gas outlet;

a differential pressure pick-up for detecting the differential pressure between the first bypass line, upstream of the first throttle, and the duct upstream of said second throttle;

a ventilation duct which is open toward the environment; and a switchover means at the first throttle for connecting the gas inlet directly with the gas outlet via a second bypass line and to bridge over the first throttle and via a third bypass line connected to the ventilation duct in a first switching position and to establish the gas flow from the gas inlet to the gas outlet via the first bypass line in a second switching position, said vaporator duct being in communication with said ventilation duct via said first bypass line and said third bypass line when said switchover means is in said first switching position such that the pressure within said first bypass line and said evaporator duct is at a almospheric pressure.

2. An anesthetic evaporator in accordance with claim 1, wherein said liquid evaporator produces anesthetic vapor, said duct receiving said anesthetic vapor from said liquid evaporator, said switchover means comprising changeover switches arranged on both sides at the first throttle, each changeover switch comprising a first switchover duct and a second switchover duct, said first switchover duct being in communication with said gas inlet when said switchover means is in said first switching position such that carrier gas is delivered from said gas inlet to said gas outlet, said second switchover duct being in communication with said first bypass line and said third bypass line when said switchover means is in said first switching position, said first switchover duct being in communication with said gas inlet and said first bypass line when said switchover means is in said second switching position such that said carrier gas mixes with said anesthetic vapor via said duct to form a carrier gas anesthetic vapor mixture, said gas outlet receiving said carrier gas anesthetic vapor mixture when said switchover means is in said second switching position, said second switchover duct being in communication with said second bypass line and said third bypass line when said switchover means is in said second switching position.

3. An anesthetic evaporator in accordance with claim 1, wherein said liquid evaporator produces anesthetic vapor, said duct receiving said anesthetic vapor from said liquid evaporator, said switchover means comprising a first switchover duct and a second switchover duct, said first switchover duct being in communication with said gas inlet when said switchover means is in said first switching position such that carrier gas is delivered from said gas inlet to said gas outlet, said second switchover duct being in communication with said first bypass line and said third bypass line when said switchover means is in said first switching position, said first switchover duct being in communication with said gas inlet and said first bypass line when said switchover means is in said second switching position such that said carrier gas mixes with said anesthetic vapor via said duct to form a carrier gas anesthetic vapor mixture, said gas outlet receiving said carrier gas anesthetic vapor mixture when said switchover means is in said second switching position, said second switchover duct being in communication with said second bypass line and said third bypass line when said switchover means is in said second switching position.

4. An anesthetic evaporator comprising:
- a gas inlet for a carrier gas;
- a gas outlet;
- a bypass line with a first throttle defining a bypass gap between said gas inlet and said gas outlet;
- a liquid evaporator with an evaporator chamber;
- a duct extending from said evaporator chamber via a second throttle to said gas outlet;
- a differential pressure pick-up having a first pneumatic connection line connected to said duct and a second pneumatic connection line connected to said bypass line for detecting the differential pressure between said bypass line, upstream of the first throttle, and said duct upstream of said second throttle;
- a ventilation duct which is open toward the environment; and
- a switchover device having a first switchover bypass line and a second switchover bypass line connected to said ventilation duct and having flow switching elements, each flow switching element switching between a first switching position and a second switching position, each flow switching element connecting said gas inlet directly with said gas outlet via said first switchover bypass line when each flow switching element is in said first switching position, each flow switching element connecting said duct downstream of said second throttle to said ventilation duct via said second switchover bypass line when each flow switching element is in said first switching position, each flow switching element connecting said bypass line upstream of said first throttle to said ventilation duct via said second switchover bypass line to bridge over said first throttle when each flow switching element is in said first switching position, each flow switching element connecting said gas inlet to said gas outlet via said bypass line such that gas flows from said gas inlet to said gas outlet via said bypass line, said duct and said bypass line being in communication with said ventilation duct when said flow switching elements are in said first switching position, wherein a pressure of said first pneumatic connection line and a pressure of said second pneumatic connection line are at atmospheric pressure when said flow switching elements are in said first switching position.

5. An anesthetic evaporator in accordance with claim 4, wherein said liquid evaporator produces anesthetic vapor, said duct receiving said anesthetic vapor from said liquid evaporator, said flow switching elements comprising changeover switches arranged on both sides of said first throttle, each changeover switch comprising a first switchover duct and a second switchover duct, said first switchover duct being in communication with said gas inlet when said flow switching elements are in said first switching position such that carrier gas is delivered from said gas inlet to said gas outlet, said second switchover duct being in communication with said bypass line and said second switchover bypass line when said flow switching elements are in said first switching position, said first switchover duct being in communication with said gas inlet and said bypass line when said flow switching elements are in said second switching position such that said carrier gas mixes with said anesthetic vapor via said duct to form a carrier gas anesthetic vapor mixture, said gas outlet receiving said carrier gas anesthetic vapor mixture when said flow switching elements are in said second switching position, said second switchover duct being in communication with said first switchover bypass line and said second switchover bypass line when said flow switching elements are in said second switching position.

6. An anesthetic evaporator in accordance with claim 4, wherein said liquid evaporator produces anesthetic vapor, said duct receiving said anesthetic vapor from said liquid evaporator, one flow switching element being located on one side of said first throttle and another flow switching element being located on another side of said first throttle, each flow switching element comprising a first switchover duct and a second switchover duct, said first switchover duct being in communication with said gas inlet and said gas outlet when said flow switching elements are in said first switching position such that carrier gas is delivered from said gas inlet to said gas outlet, said second switchover duct being in communication with said second switchover bypass line and said bypass line when said flow switching elements are in said first switching position, said first switchover duct being in communication with said gas inlet and said bypass line when said flow switching elements are in said second switching position such that said carrier gas mixes with said anesthetic vapor via said duct to form a carrier gas anesthetic vapor mixture, said gas outlet receiving said carrier gas anesthetic vapor mixture when said flow switching elements are in said second switching position, said second switchover duct being in communication with said first switchover bypass line and said second switchover bypass line when said flow switching elements are in said second switching position.

7. An anesthetic evaporator operation process comprising:
- connecting a gas inlet to a carrier gas source;
- providing a gas outlet;
- providing a bypass line with a first throttle defining a bypass gap between the gas inlet and the gas outlet;
- providing a liquid evaporator with an evaporator chamber;
- providing a duct extending from the evaporator chamber via a second throttle to the gas outlet;
- providing a differential pressure pick-up between the bypass line, upstream of the first throttle, and the duct upstream of the second throttle for detecting the differential pressure between a first pneumatic connection to the bypass line, upstream of the first throttle, and a second pneumatic connection to the duct upstream of the second throttle;
- providing a ventilation duct which is open toward the environment; and
- providing a switchover device having a first switchover bypass line and a second switchover bypass line connected to the ventilation duct and having flow switching elements;
- operating the switchover device in a first switching position connecting the gas inlet directly with the gas outlet via the first switchover bypass line and connecting the duct downstream of the second throttle to the ventilation duct via the second switchover bypass line and connecting the bypass line upstream of the first throttle to the ventilation duct via the second switchover bypass line to bridge over the first throttle; and operating the switchover device in a second switching position to establish the gas flow from the gas inlet to the gas outlet via the bypass line.

8. An anesthetic evaporator operation process according to claim 7, further comprising:

calibrating the differential pressure pick-up during operation in the first switching position with each of the first pneumatic connection and second pneumatic connection open toward the ambient atmosphere and at the prevailing pressure of the ambient atmosphere.

9. An anesthetic evaporator operation process according to claim 8, wherein the flow switching elements comprise changeover switches arranged on both sides of the first throttle.

10. An anesthetic evaporator operation process according to claim 7, wherein said liquid evaporator produces anesthetic vapor, said duct receiving said anesthetic vapor from said liquid evaporator, said switchover device comprising a first switchover duct and a second switchover duct, said first switchover duct being in communication with said gas inlet and said gas outlet when said switchover device is in said first switching position such that carrier gas is delivered from said gas inlet to said gas outlet, said second switchover duct being in communication with said first switchover bypass line and said second switchover bypass line when said switchover device is in said first switching position, said first switchover duct being in communication with said gas inlet and said bypass line when said switchover device is in said second switching position such that said carrier gas mixes with said anesthetic vapor delivered via said duct to form a carrier gas anesthetic vapor mixture, said gas outlet receiving said carrier gas anesthetic vapor mixture when said switchover device is in said second switching position, said second switchover duct being in communication with said first switchover bypass line and said second switchover bypass line when said switchover device is in said second switching position.

11. An anesthetic evaporator in accordance with claim 1, further comprising a heater, said liquid evaporator containing liquid anesthetic, said heater heating said liquid anesthetic to form anesthetic vapor, said duct receiving said anesthetic vapor from said liquid evaporator, said first bypass line receiving said anesthetic vapor from said duct when said switchover means is in said second switching position.

12. An anesthetic evaporator in accordance with claim 11, further comprising a shut-off valve and a proportional valve, wherein said shut-off valve and said proportional valve are connected to said duct, said shut-off valve and said proportional valve controlling a flow of said anesthetic vapor in said duct.

13. An anesthetic evaporator in accordance with claim 1, wherein said differential pick-up has a first pneumatic connection line connected to said duct and a second pneumatic connection line connected to said first bypass line.

14. An anesthetic evaporator in accordance with claim 4, further comprising a heater, said liquid evaporator containing liquid anesthetic, said heater heating said liquid anesthetic to form anesthetic vapor, said duct receiving said anesthetic vapor from said liquid evaporator, said bypass line receiving said anesthetic vapor from said duct when said flow switching elements are in said second switching position.

15. An anesthetic evaporator in accordance with claim 14, further comprising a shut-off valve and a proportional valve, wherein said shut-off valve and said proportional valve are connected to said duct, said shut-off valve and said proportional valve controlling a flow of said anesthetic vapor in said duct.

16. An anesthetic evaporator in accordance with claim 15, wherein said flow switching elements are parallel to said bypass gap.

17. An anesthetic evaporator in accordance with claim 7, further comprising:

providing a heater, said liquid evaporator containing liquid anesthetic;

heating said liquid anesthetic in said liquid evaporator with said heater to form anesthetic vapor, said duct receiving said anesthetic vapor from said liquid evaporator, said bypass line receiving said anesthetic vapor from said duct when said switchover device is in said second switching position.

18. An anesthetic evaporator in accordance with claim 17, further comprising:

providing a shut-off valve;

providing a proportional valve;

connecting said shut-off valve and said proportional valve to said duct, said shut-off valve and said proportional valve controlling a flow of said anesthetic vapor in said duct.

19. An anesthetic evaporator in accordance with claim 7, wherein said duct and said bypass line are in communication with said ventilation duct when said switching device is in said first switching position, wherein a pressure of said first pneumatic connection and a pressure of said second pneumatic connection are at atmospheric pressure when said flow switching elements are in said first switching position.

20. An anesthetic evaporator operation process according to claim 7, wherein said liquid evaporator produces anesthetic vapor, said duct receiving said anesthetic vapor from said liquid evaporator, said switchover device comprising a first changeover switch located on one side of said first throttle and a second changeover switch located on another side of said first throttle, said first changeover switch and said second changeover switch comprising a first switchover duct and a second switchover duct, said first switchover duct being in communication with said gas inlet and said gas outlet when said switchover device is in said first switching position such that carrier gas is delivered from said gas inlet to said gas outlet, said second switchover duct being in communication with said first switchover bypass line and said second switchover bypass line when said switchover device is in said first switching position, said first switchover duct being in communication with said gas inlet and said bypass line when said switchover device is in said second switching position such that said carrier gas mixes with said anesthetic vapor delivered via said duct to form a carrier gas anesthetic vapor mixture, said gas outlet receiving said carrier gas anesthetic vapor mixture when said switchover device is in said second switching position, said second switchover duct being in communication with said first switchover bypass line and said second switchover bypass line when said switchover device is in said second switching position.

* * * * *